United States Patent [19]

Tabushi et al.

[11] Patent Number: 4,564,690

[45] Date of Patent: Jan. 14, 1986

[54] MACROCYCLIC COMPOUNDS

[75] Inventors: Iwao Tabushi; Yoshiaki Kobuke, both of Kyoto, Japan

[73] Assignee: Mitsubishi Chemical Industries Limited, Tokyo, Japan

[21] Appl. No.: 447,443

[22] Filed: Dec. 6, 1982

Related U.S. Application Data

[63] Continuation of Ser. No. 202,614, Oct. 31, 1980, abandoned.

[30] Foreign Application Priority Data

Nov. 14, 1979 [JP] Japan .................. 54-148136

[51] Int. Cl.$^4$ ............... C07C 61/00; C07D 323/00; C07F 9/38
[52] U.S. Cl. ............... 549/352; 260/239 BC; 260/464; 260/926; 260/500.5 H; 260/502.4 P; 260/502.5 C; 260/503; 549/11; 560/127; 562/509
[58] Field of Search .............. 562/509; 560/127; 260/503, 502.4 P, 502.5 C, 500.5 H, 239 BC, 926, 464; 549/352, 11

[56] References Cited

FOREIGN PATENT DOCUMENTS 141295 12/1978 Japan .................. 562/509

OTHER PUBLICATIONS

Voegtle, Synthesis, 1972, 543, Abstract only.

*Primary Examiner*—Robert Gerstl
*Attorney, Agent, or Firm*—Jordan B. Bierman

[57] ABSTRACT

A macrocyclic compound represented by the following general formula:

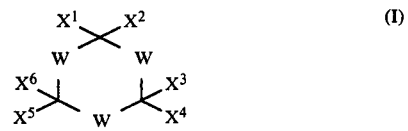

(I)

and a process for preparing thereof which comprises reacting an α,ω-dihalogenated hydrocarbon and an active methylene compound with a base in a solvent to obtain a macrocyclic compound represented by the following general formula (II):

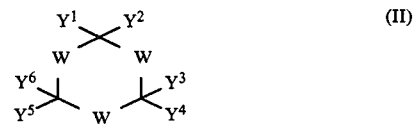

(II)

and then inducing the functional group of $Y^1$, $Y^3$ and $Y^5$ by means of a hydrolysis, oxidation or such, and an uranyl ion capturing agent comprising a polymer chemically bonded to a functional group in a macrocyclic compound and preparation thereof.

11 Claims, No Drawings

MACROCYCLIC COMPOUNDS

This application is a continuation of application Ser. No. 202,614, filed 10/31/80 now abandoned.

BACKGROUND OF THE INVENTION

FIELD OF THE INVENTION

This invention relates to the novel macrocyclic compounds, preparation thereof, an uranyl ion capturing agent comprising a polymer chemically bonded to a functional group in a macrocyclic compound and preparation thereof.

Recently, many efforts are being made in various fields of industry for recovering the uranyl ions ($UO_2^+$) from seawater, dam waste water, poor ore and other sources. Uranyl ions are attracting attention of the researchers as a promising source of atomic energy in these days of "oil crises", and many advanced countries are struggling with devicing a method for recovering the uranyl ions from seawater which may well be said inexhausible.

As a means for extracting the uranyl ions from seawater, there is a known method using a titanic acid adsorbent, but this method has a defect in that some of the adsorbent is lost by such as flowing out or so in use. Uranyl ions exist in seawater at a concentration of approximately 3.3 ppb in the form of a stable carbonate complex salt, so in order to extract such uranyl ions from seawater on an industrial scale, it is necessary to use an extracting agent which has ability of extracting the uranyl ions from the carbonate complex salt easily and also of selectively extracting the uranyl ions from other metal ions such as magnesium ions. In the course of the study, from said viewpoint, on the cyclic compounds having an ability to capture the metal ions, the present inventors had found that when a macrocyclic hexaketone or a polymer having such macrocyclic hexaketone as functional group is used in place of said titanic acid adsorbent, it is possible to extract the uranyl ions easily from the carbonate complex salt and to capture the uranyl ions selectively and stably too, and a patent application is filed for this finding (Japanese Patent Application No. 053025/1979).

As a result of further studies on the cyclic compounds having an ability to capture the uranyl ions, we have now succeeded in developing a new uranyl ion capturing agent which, as compared with previously proposed uranyl ion capturing agent composed of a macrocyclic hexaketone or a polymer having such macrocyclic hexaketone as functional group, is far less interfered with other metals or anions in capturing the uranyl ions and which can be also synthesized in a more simple process.

SUMMARY OF THE INVENTION

It is an object of the present invention to provide a novel macrocyclic compounds and a process for preparing thereof.

An another object of the invention is provide an uranyl ion capturing agent comprising a polymer chemically bonded to a functional group in a macrocyclic compound and a process for a preparing thereof.

DETAILED DESCRIPTION OF PREFERRED EMBODIMENT

The present invention provides the macrocyclic compounds represented by the following general formula (I):

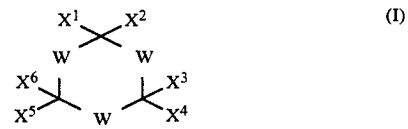

[wherein $X^1$, $X^3$ and $X^5$ may be same or different and represent a functional group selected from the group consisting of —COOH,

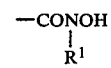

(wherein $R^1$ is a hydrogen atom, an alkyl group or an aromatic group), —$SO_3H$, —$PO_3H$ and —$PO_4H_2$; $X^2$, $X^4$ and $X^6$ may be same or different and represent respectively a functional group defined above or a group selected from the group consisting of hydrogen atom, alkyl group, aromatic group, —$COOR^2$ (where $R^2$ is an alkyl group or an aromatic group),

(where $R^{11}$ and $R^{12}$ may be same or different and represent the same as $R^1$), —$COR^1$ (where $R^1$ is as defined above), —CN, —$SOR^2$ (where $R^2$ is as defined above),

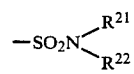

(where $R^{21}$ and $R^{22}$ may be same or different and represent the same as $R^2$), —$SO_2R^2$ (where $R^2$ is as defined above), —$NO_2$, —$PO_3R^{21}R^{22}$ (where $R^{21}$ and $R^{22}$ are as defined above and they may be same or different) and —$PO_4R^{21}R^{22}$ (where $R^{21}$ and $R^{22}$ are as defined above and they may be same or different); and W is a divalent group selected from the class consisting of methylene, —$(CH_2)_n$— (where n is 2 to 18) or those of methylene in which 1 to 9 pieces of $CH_2$ have been replaced by the hetero-atoms an, alicyclic group, an aromatic group, and a heterocyclic group] and a process for the preparation thereof, as well as an uranyl ion capturing agent composed of a compound comprising a polymer chemically bonded to at least one of the groups of $X^2$, $X^4$ and $X^6$ of a macrocyclic compound represented by the formula (I) and a process for the preparation thereof.

The novel macrocyclic compounds according to this invention are the compounds represented by the formula (I), and such compounds are diversified according to what are to be represented by $X^1$-$X^6$ and W in said formula. It is specified in this invention that the groups represented by $X^1$, $X^3$ and $X^5$ in the formula (I) are to be selected from the group consisting of —COOH, $$-\text{CONOH} \atop R^1$$

(where $R^1$ is as defined above), $-SO_3H$, $-PO_3H_2$ and $-PO_4H_2$, $X^1$, $X^3$ and $X^5$ require three free radicals on the plane as effective ligands for the uranyl ions. Also, the groups represented by $X^2$, $X^4$ and $X^6$ in the formula are defined to be the functional groups specified for $X^1$, $X^3$ and $X^5$ or the groups selected from the group consisting of hydrogen atom, alkyl group, etc, because the active methylene compounds used as starting material for synthetis of a macrocyclic compound of the formula (I) are easily available and also because they are easily reacted with the α,ω-halogenated hydrocarbons used as another starting material in this invention. $R^1$, $R^{11}$ and $R^{12}$ in the definitions of $X^1$–$X^6$ represent respectively hydrogen atom, an alkyl group or an aromatic group, while $R^2$, $R^{21}$ and $R^{22}$ represent an alkyl group or an aromatic group. The alkyl group mentioned above may be selected from the lower alkyl groups such as methyl, ethyl, propyl, butyl, etc., or higher alkyl groups such as stearyl, lauryl, etc., while the aromatic group may be, for example,

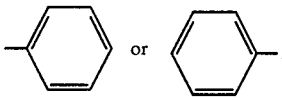

W is basically methylene—$(CH_2)_n$— where n is 2 to 18, because when n is 1 the reaction with the active methylene compound becomes difficult to carry out and when n is 19 or more, the halogenated hydrocarbons become hard to gain and also become expensive. Thus, n is defined to be a number of from 2 to 18, but it is most desirable that n is around 8 because of the advantage in creating a suitable space for accommodating the uranyl ions. W may be also selected from those of methylene in which 1 to 9 pieces of $CH_2$ have been replaced by the hetero-atoms including oxygen atom, nitrogen atom and sulfur atom, or from the class of the alicyclic group such as cyclohexylene, norbornylene, etc., or aromatic group such as phenylene, xylylene, etc., or the class of the heterocyclic group such as furandiyl pyrroldiyl, pyrandiyl, piperadinediyl, dioxanediyl, thiophenediyl, etc. It is possible to synthesis various types of macrocyclic compounds by suitably selecting these groups.

The macrocyclic compounds of this invention have characteristically a structure in which six hetero-atoms such as oxygen atom, nitrogen atom and sulfur atoms are arranged on a substantially same plane, facing inwardly of the ring, at suitable distances from the center of the cyclic molecules. In other structure of the compounds of this invention, they have a ring size sufficient to allow the uranyl ion in the molecule, maintaining stability of the ring structure.

As examples of the macrocyclic compounds represented by the above-shown general formula (I), the following may be cited: 1,1,10,10,19,19-hexacarboxy-cycloheptacosane, 1,10,19-tricarboxy-1,10,19-tricarboethoxy-cycloheptacosane, 1,10-19-tricarboxy-1,10,19-tricyano-4,7,13,16,22,25-hexaoxacycloheptacosane, 1,10-dicyano-19-carboethoxy-1,10,19-tricarboxy-4,7,13,16,22,25-hexaoxacycloheptacosane, 1,9-dicyano-17-acetyl-1,9,17-tricarboxy-cyclotetracosane, 3,14,25-tris(methylsulphoxy)-3,14,25-tricarboxy-[5,5,5]tris-paracyclophane, and 1,10,19-tricarboethoxy-cycloheptacosane-1,10,19-triphosphoric acid. Among these compounds, the one in which $X^1$–$X^6$ is —COOH and W is —$(CH_2)_8$—, that is, 1,1,10,10,19,19-hexacarboxy-cycloheptacosane represented by the following formula:

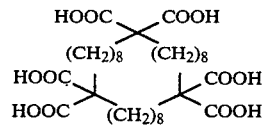

has a particularly excellent ability to extract the uranyl ions from a carbonate complex salt and capture them.

The process for preparing the macrocyclic compounds represented by the above-shown general formula (I) is now described.

Firstly, an α,ω-dihalogenated hydrocarbon and an active methylene compound are reacted with a base in a solvent to give a macrocyclic compound of the following formula (II):

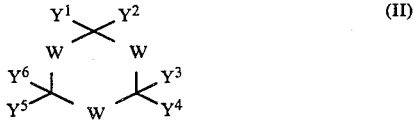

[wherein $Y^1$, $Y^3$ and $Y^5$ may be same or different and represent respectively a functional group selected from the group consisting of —$COOR^2$ (where $R^2$ is an alkyl group or an aromatic group), —CN, —$SOR^2$ (where $R^2$ is as defined above), —$PO_3R^{21}R^{22}$ (where $R^{21}$ and $R^{22}$ may be same or different and represent the same as $R^2$) and —$PO_4R^{21}R^{22}$ (where $R^{21}$ and $R^{22}$ are as defined above and they may be same or different); $Y^2$, $Y^4$ and $Y^6$ may be same or different and represent respectively a functional group defined above or a group selected from the group consisting of hydrogen atom, alkyl group, aromatic group,

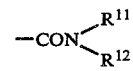

(where $R^{11}$ and $R^{12}$ may be same or different and represent respectively hydrogen atom, an alkyl group or an aromatic group), —$COR^1$ (where $R^1$ is same as $R^{11}$ or $R^{12}$),

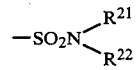

(where $R^{21}$ and $R^{22}$ are as defined above and they may be same or different), —$SO_2R^2$ (where $R^2$ is as defined above) and —$NO_2$; and W is a divalent group selected from the class consisting of methylene, —$(CH_2)_n$— (where n is 2 to 18) or those of methylene in which 1 to 9 pieces of $CH_2$ have been replaced by the heteroatoms, an alicyclic group, an aromatic group, and a heterocyclic group] and thus obtained compound is then subjected to a suitable treatment such as hydrolysis, oxidation, etc., to convert the functional group(s) of $Y^1$, $Y^3$ and $Y^5$ into one selected from the group consisting of —COOH, $$-\underset{\underset{R^1}{|}}{\text{CONOH}}$$

(where $R^1$ is as defined above), $-SO_3H$, $-PO_3H_2$ and $-PO_4H_2$, thereby to give a macrocyclic compound of the general formula (I).

The term "α,ω-dihalogenated hydrocarbon" is used here to refer to a hydrocarbon having at its both terminals a halogen such as chloro, bromo, iodo, etc. Such halogen may be replaced by methane sulfonate, p-toluene sulfonate or p-bromosulfonate. As examples of such hydrocarbons, there may be cited the α,ω-dihalogenated straight-chain hydrocarbons such as 1,4-dichlorobutane, 1,4-dibromobutane, 1,4-diiodobutane, 1,5-dichloropentane, 1,5-dibromopentane, 1,5-diiodopentane, 1,6-dichlorohexane, 1,6-dibromohexane, 1,6-diiodohexane, 1,7-dichloroheptane, 1,7-dibromoheptane, 1,7-diiodoheptane, 1,8-dichlorooctane, 1,8-diiodooctane, 1,9-dichlorononane, 1,9-diiodononane, 1,10-dichlorodecane, 1,10-diiododecane, 1,8-dibromooctane, 1,9-dibromononane, 1,10-dibromodecane, 1,12-diiodododecane, 1,14-dichlorotetradecane, 1,16-dibromohexadecane and 1,18-dibromooctadecane, the compounds containing the hetero-atoms such as bis(2-bromoethoxy)ethane and bis(4-chloro-n-butyl)ether, halogenated aromatic hydrocarbons such as xylenedibromide, bis(chloromethyl)durene and bis(chloromethyl) mesitylene, and alicyclic hydrocarbons such as 1,4-dibromocyclohexane and 2,5-dibromobicyclo[2,2,1]heptane.

Various kinds of active methylene compounds may be used depending on the type of the macrocyclic compound to be prepared. Such active methylene compounds include, for example, dimethyl-and diethyl malonate, ethyl t-butyl malonate, methyl-and ethyl cyanoacetate, methyl-and ethyl nitroacetate, methyl-and ethyl acetoacetate, ethyl benzoylacetate, methylmethylthiomethylsulfoxide and ethyl diethylphosphonoacetate.

As the base used in the above-said reaction of this invention, it is possible to use a metallic hydride such as sodium hydride or potassium hydride, a metallic alkoxide such as sodium ethylate or potassium t-butoxide, or an organic metal compound such as methylmagnesium bromide or n-butyl-lithium. It is also possible to use such compounds as sodium amide, lithiumdiisopropylamide, sodium naphthalenide, sodium salt of dimethyl sulfoxide and the like.

The solvent used in the reaction may be properly selected from the alcohol solvents such as ethanol, methanol, etc., ether solvents such as ether, tetrahydrofuran, diethyleneglycol dimethyl ether, etc., aromatic hydrocarbons such as benzene, toluene, etc., and polar non-protonic solvents such as dimethylformamide, dimethyl sulfoxide, etc.

The reaction conditions of the reaction are not subject to any particular restrictions and may be optionally selected, but usually the reaction is carried out at a temperature within the range of from room temperature to the reflux temperature of the solvent used for 1 to 20 hours.

As described above, in the production of a macrocyclic compound of the general formula (I), first an α,ω-dihalogenated hydrocarbon and an active methylene compound, such as cited above, are reacted. This reaction may not necessarily be of a single stage but may be conducted repeatedly in two or more stages if required.

For instance, in case a halogen is present at the α,ω-position of the compound obtained from the reaction of said α,ω-dihalogenated hydrocarbon and active methylene compound, an active methylene can be further reacted to said compound. By repeating this reaction for a required number of times, it is possible to produce a macrocyclic compound of the formula (II). This compound itself can be used as an uranyl ion capturing agent, but in order to enhance the uranyl ion capturing activity, such compound is further altered into a carboxylic acid, a hydroxamic acid, an amide, a sulfonic acid, a sulfonic acid amide or the like by a hydrolysis, oxidation or other means. For instance, esters, nitriles, ketones, phosphonic acid esters and the like can be converted into a carboxylic acid, amide, phosphonic acid, etc., by an ordinary hydrolysis reaction using base or acid and further led into a hydroxamic acid by an ordinary chemical reaction. Also, sulfides and sulfoxides can be oxidized into a sulfonic acid by using potassium permanganese or hydrogen peroxide, thus producing various types of macrocyclic compounds according to the purpose of use.

For instance, when 1,8-dibromooctane and diethyl malonate are reacted with a base in a solvent, we obtained a hexacarboxylic acid hexaethyl ester represented by the following chemical formula:

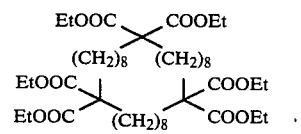

and hydrolysis of this compound gives 1,1,10,10,19,19-hexacarboxycycloheptacosane having the following chemical formula:

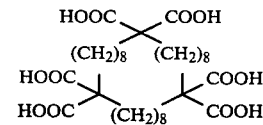

Explanation is now given to the uranyl ion capturing agent formed from a compound comprising a polymer chemically bonded to the functional groups in a macrocyclic compound of the aboveshown general formula (I). The polymer used in this invention for said purpose may be of any type provided that the substituent in the polymer is reactable with and chemically bondable to the functional groups in a macrocyclic compound of the general formula (I), and it is possible to use a variety of synthetic polymers such as polystyrene, polyethylene, polypropylene, polyacrylonitrile, polyacrylic acid, polyvinyl alcohol, polyvinyl chloride, polybutadiene, nylon, tetron, polyurethane, polyamino-acids, polyethyleneimine, polyethylene oxide, etc., natural or semisynthetic polymers such as wool, cotton, silk, etc., and the substances derived from such polymers by a chemical reaction. In case the functional group in a macrocyclic compound of the general formula (I) is $-CN$ or $-NO_2$, the polymer can not be directly bonded to these groups, but in this case, desired polymer bonding can be accomplished by the chemical transformation of these functional group by reduction, hydrolysis or other treatment, followed by bonding it to a polymer having a pertinent substituent. Among said polymers, the styrene type polymers prove to be most convenient for the reaction. For instance, a chloromethyl group may be introduced into a styrene type polymer and, after converting it into a proper functional group such as aminomethyl group, the polymer may be subjected to a condensation reaction with 1,1,10,10,19,19-hexacarboxycycloheptacosane, giving an uranyl ion capturing agent made of a compound having the following formula:

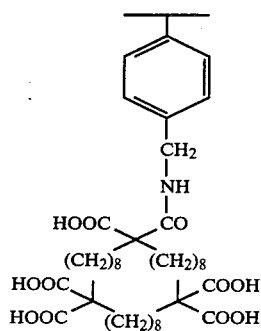

This uranyl ion capturing agent can be used in the form of resin, fiber or such, so it has an advantage that it suffers less loss in use than the macrocyclic compounds represented by the general formula (I).

We will now describe the process for preparing an uranyl ion capturing agent made of a compound comprising a polymer chemically bonded to at least one group of $X^2$, $X^4$ or $X^6$ in a hexacarboxylic acid of the general formula (I).

A macrocyclic compound of the general formula (III):

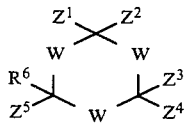

[wherein $Z^1$ to $Z^6$ may be same or different but at least one of them represents a functional group selected from the group consisting of —COCl, —COOR$^1$ (where R$^1$ is a hydrogen atom, an alkyl group or an aromatic group), —COOCOR$^3$ (where R$^3$ is an alkyl group, a halogenated alkyl group or an aromatic group), —COSR$^1$ (where R$^1$ is as defined above), —CONHR$^1$ (where R$^1$ is as defined above), —COCH$_2$R$^1$ (where R$^1$ is as defined above), —SOCH$_2$R$^1$ (where R$^1$ is as defined above), —SO$_2$R$^1$ (where R$^1$ is as defined above), —SO$_2$Cl, —SO$_3$R$^1$ (where R$^1$ is as defined above),

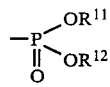

(where R$^{11}$ and R$^{12}$ may be same or different and represent respectively a hydrogen atom, an alkyl group or an aromatic group) and

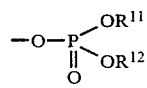

(where R$^{11}$ and R$^{12}$ are as defined above and they may be same or different), and the remainder represent a group selected from the group consisting of hydrogen atom, alkyl group, aromatic group, —SOR$^2$ (where R$^2$ is an alkyl group or an aromatic group),

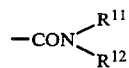

(where R$^{21}$ and R$^{22}$ may be same or different and represent the same as R$^1$), —COR$^1$ (where R$^1$ is as defined above), —CN,

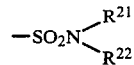

(where R$^{21}$ and R$^{22}$ may be same or different and represent the same as R$^1$), —NO$_2$ and

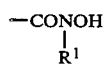

(where R$^1$ is as defined above); $Z^1$, $Z^3$ and $Z^5$ represent respectively a functional group selected from the group consisting of —COOH, —COOR$^2$ (where R$^2$ is as defined above),

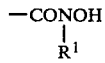

(where R$^1$ is as defined above), —CN,

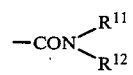

(where R$^{21}$ and R$^{22}$ may be same or different and represent the same as R$^2$), —SO$_3$H, —SOR$^2$ (where R$^2$ is as defined above),

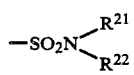

(where R$^{21}$ and R$^{22}$ may be same or different and represent the same as R$^2$), —SO$_2$R$^2$ (where R$^2$ is as defined above), —PO$_3$H$_2$, —PO$_4$H$_2$,

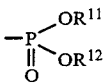

(where R$^{21}$ and R$^{22}$ may be same or different and represent the same as R$^2$) and

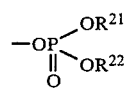

(where R$^{21}$ and R$^{22}$ may be same or different and represent the same as R$^2$); and W is a divalent group selected from the class consisting of methylene, —(CH$_2$)$_n$—

(where n is 2 to 18) or those of methylene in which 1 to 9 pieces of $CH_2$ have been replaced by the hetero-atoms, an alicyclic group, an aromatic group, and a heterocyclic group] and a polymer having a substituent are reacted in a solvent and, if necessary, the reaction product is further subjected to a treatment such as hydrolysis, oxidation, etc., to transform the functional group(s) of $Z^1$, $Z^3$ and $Z^5$ in a macrocyclic compound of the formula (III) into a functional group selected from the group consisting of —COOH,

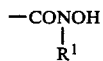

(where $R^1$ is as defined above), —$SO_3H$, —$PO_3H_2$ and —$PO_4H_2$, thereby, to prepare an uranyl ion capturing agent made of a compound comprising a polymer chemically bonded to at least one group of $X^2$, $X^4$ or $X^6$ in a macrocyclic compound of the general formula (I). The reaction conditions are not subject to any specific restrictions, but the following method allows preparation of the objective agent at very high efficiency: A polymer, for instance a styrene polymer having an aminomethyl group introduced into the side chains, and a macrocyclic compound of the formula (I) having at least one functional group thereof transformed into an acid chloride are subjected to an acylation reaction in a solvent in the presence of a base. The solvent used here may be of any type provided that it is capable of dissolving the macrocyclic compound of the general formula (I) and won't retard the acylation reaction. For example, the solvent may be an ether type solvent such as ether, tetrahydrofuran, diethylene glycol dimethyl ether, etc., an aromatic hydrocarbon such as benzene, toluene, etc., or other compound such as dimethylformamide, dimethyl sulfoxide, etc. Also, an aromatic amine such as pyridine may be used directly as solvent. What can be used as the base is one which promote the acylation reaction, such as $K_2CO_3$, $Na_2CO_3$, KOH, NaOH, pyridine or triethylamine. Other reaction conditions may be suitably selected to suit the situation and are not limitative.

Having the above-described features, the present invention can produce the following effects. Firstly, the uranyl ion capturing agent according to this invention is free of the problem of adsorbent efflux which is often encountered in case of using the conventional titanic acid adsorbents. Also, the uranyl ion capturing agent according to this invention is particularly effective as a selective ligand for the uranyl ions owing to the six hetero-atoms including oxygen atom, nitrogen atom and sulfur atom existing in the cyclic molecules and is also far less interfered with other metals or anions as compared with the heavy metal capturing agents comprising the polymers having aforementioned macrocyclic hexaketones as functional group. Further, owing to a wide diversity in the type of functional groups of the macrocyclic compounds represented by the formula (I), the product of this invention is capable of not only capturing the uranyl ions directly from seawater but also capturing the uranyl ions from other sources such as waste water from nuclear reactors, secondary concentrated solutions, poor ore, etc. Moreover, the uranyl ion capturing agent according to this invention can be produced at low cost since the synthesizing process thereof is relatively simple.

The following examples are intended to illustrate the present invention in further details.

EXAMPLE 1

Preparation of bis(ω-iodooctyl)malonic acid diethyl ester 0.29 g (1.8 mmol) of diethyl malonate was dissolved in 20 ml of tetrahydrofuran dried with metallic sodium, and to this solution was added 0.093 g (1.9 mmol) of sodium hydride followed by 30-minutes reflux under heating. To this reaction solution was added dropwise 2.86 g (10.5 mmol) of 1,8-dibromooctane, effecting reflux under heating for 1.5 hours. This reaction solution was further added with 0.093 g (1.9 mmol) of sodium hydride and refluxed for 2 hours. Tetrahydrofuran was distilled off and the residue was cooled to room temperature, added with 1N hydrochloric acid until the litmus paper came to show acidity and then extracted three times with 20 ml of ether. After drying the extract over anhydrous sodium sulfate, ether was distilled off and then excess 1,8-dibromooctane was also distilled off under reduced pressure. The oily residue was dissolved in 20 ml of 2-butanone, added with 2 g (17 mmol) of sodium iodide and refluxed under heating for 10 hours. After distilling off most of 2-butanone, the solution was added with 20 ml of ether and washed twice with 5 ml of a saturated saline solution. The ether layer was dried over anhydrous sodium sulfate and the oily residue, from which ether has been removed, was passed through a silica gel-packed column and eluted with a 3:1 hexane/benzene mixture to obtain 0.37 g of bis(ω-iodooctyl)malonic acid diethyl ester,

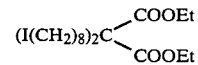

(yield: 32%).

Preparation of α,ω-bisdiethylmalonyloctane 4.16 g (0.18 mol) of metallic sodium was added gradually and dissolved in 75 ml of dry ethanol, and to this solution was further added 32 g (0.2 mol) of diethyl malonate and refluxed under heating for 30 minutes. Then 12.2 g (0.045 mol) of 1,8-dibromooctane was added dropwise slowly to said solution, continuing reflux under heating for 4 hours. After completion of the reaction, aqueous solution of $NH_4Cl$ was added to the reaction solution to neutralize it and then extracted three times with 50 ml of ether. After drying the extract over anhydrous sodium sulfate, ether was distilled off and the obtained oily product was distilled under reduced pressure to obtain 11.5 g of α,ω-bisdiethylmalonyloctane (59% yield) as a colorless liquid. The results of the property analyses of this compound were as shown below.

Boiling point: 194°–196° C./0.4 mmHg. Infrared absorption spectrum (liquid film method): 1720 cm$^{-1}$ (C=O of ester).

Proton nuclear magnetic resonance spectrum (Solvent: $CCl_4$, internal standard $Si(CH_3)_4$): δ: 1.1–1.4 (m, 24H), 1.81 (m, 4H), 3.16 (t, 2H), 4.14 (q, 8H).

Preparation of hexacarboxylic acid hexaethyl ester 3.82 g (6 mmol) of bis(ω-iodooctyl)malonic acid diethyl ester and 2.59 g (6 mmol) of α,ω-bisdiethylmalonyloctane, both obtained in the manner described above, were dissolved in 1,200 ml of dry tetrahydrofuran, and this solution was further added with 1.30 g (27 mmol) of potassium hydride and refluxed under heating for 14 hours. After neutralizing the solution with 1N hydrochloric acid, tetrahydrofuran was distilled off and the residue was separated by silica gel-packed column chromatography by using chloroform-n-hexane (2:1) as eluent to obtain 1.56 g of hexacarboxylic acid hexaethyl ester in the form of white solid (yield: 32%). The property analyses of this compound gave the following results.

Solubility: Sparingly soluble in water but easily soluble in chloroform, ether, benzene and dimethylformamide.

Melting point: 59° C.

Infrared absorption spectrum (KBr tablet method): 1710 cm$^{-1}$ (C=O of ester).

Proton nuclear magnetic resonance spectrum (solvent: CDCl$_3$, internal standard Si(CH$_3$)$_4$) δ: 1.0-1.5 (m, 54H), 1.6-2.0 (m, 12H), 4.1 (q, 12H).

Mass spectrum (methyl ester) m/e: 726 (M+), 694, 662, 634, 602.

Elemental analysis: C: 66.93 (calcd. 66.64) H: 9.61 (calcd. 9.69).

Preparation of 1,1,10,10,19,19-hexacarboxy-cycloheptacosane 87 mg (0.135 mmol) of the hexacarboxylic acid hexaethyl ester obtained in the above-said example was added to 10 ml of methanol containing 513 mg (7.7 mmol) of potassium hydroxide and refluxed under heating for 22 hours. After the reaction has ended, methanol was distilled off and the residue was washed three times with 20 ml of ether and the water layer was made acidic with 1N hydrochloric acid and extracted five times with 100 ml of ether, and the extract was dried over anhydrous sodium sulfate. Ether was distilled off to obtain 54 mg of a white solid product (yield: 78%). The property analyses of this compound gave the following results.

Solubility: Sparingly soluble in water, chloroform and benzene but easily soluble in ether and dimethylformamide.

Melting point: 210° C.

Infrared absorption spectrum (KBr tablet method): absorption at 1690 cm$^{-1}$ (C=O of carboxylic acid).

Mass spectrum m/e: 641 (M+1).

Elemental analysis: C 61.63 (calcd. 61.66), H 8.49 (calcd. 8.47).

From the above analytical results, the obtained compound was identified as 1,1,10,10,19,19-hexacarboxycycloheptacosane of the following formula:

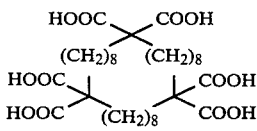

Preparation of aminomethylpolystyrene 200 ml of dimethylformamide was added to a mixture of chloromethylpolystyrene (Cl content: 0.1 mol equivalent, mfd. by Mitsubishi Chemical Industries Ltd.), 29.4 g (0.2 mol) of phthalimide and 27.6 g (0.2 mol) of anhydrous potassium carbonate, and the mixed solution was heated gradually from room temperature to 140° C. and maintained at 140° C. for 8 hours. The solution was than filtered and the precipitate was washed well with hot water. The filtered out solid was added with 50 ml of hydrazine hydrate and 50 ml of water and, after 1-hour standing at room temperature, heated to 60° C. and stirred for 3.5 hours. The reaction product was filtered and washed with hot water. The results of the property analyses of this polymer were as shown below.

Infrared absorption spectrum (KBr tablet method): 3,400 cm$^{-1}$ (NH stretching vibration), 1,600 cm$^{-1}$ (NH deformation vibration).

Elemental analysis: N: 2.45.

Example in Chemical bonding of aminomethylpolystyrene to 1,1,10,10,19,19-hexacarboxy-cycloheptacosane 128 mg (0.2 mmol) of hexacarboxylic acid and 20.6 mg (0.1 mmol) of dicyclohexylcarbodiimide were added to 58.5 mg of the aminomethylpolystyrene (amino group content: 0.1 mmol equivalent) obtained in the above-said example, and the mixture was stirred in 2 ml of dimethylformamide for 5 hours. Thereafter, the reaction solution was filtered, washed with methanol and dried to obtain 68 mg of a compound. As the IR absorption spectrum of this compound showed absorption attributable to carboxylic acid at 1700 cm$^{-1}$ and absorption of acid amide at 1740 cm$^{-1}$, this compound was identified as a substance defined by the following formula (IV):

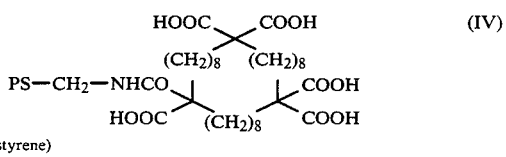

(PS: Polystyrene)

Uranyl ion capturing test 1

Each 5 ml of an ether solution (4.2×10$^{-3}$ mol/l) of the 1,1,10,10,19,19-hexacarboxy-cycloheptacosane obtained as said above was mixed with each of 1 ml of an aqueous solution prepared by dissolving UO$_2$(OCOCH$_3$)$_2$ in distilled water and 1 ml of each of the aqueous uranium solutions containing the carbonate ions, magnesium ions and sodium ions, respectively, in the same concentrations as seawater, and each mixed solution was magnetically stirred and the uranium concentration in the solution after the lapse of a given period of time was measured to give the following the results.

| Type of ions added | Concentration (g/l) | pH | Uranium concentration (ppm) | | Contact time (hr) | Capturing rate (%) |
|---|---|---|---|---|---|---|
| | | | Initial concentraton | Residual conc. | | |
| None | | 8.2 | 8.0 | 0.82 | 1.5 | 90 |
| Mg++ | 1.29 | 8.1 | 7.5 | 0.18 | 1.0 | 98 |
| Na+ | 10.78 | 8.0 | 7.7 | 0.08 | 1.0 | 99 |
| CO$_3$-- | 0.14 | 8.0 | 9.6 | 1.20 | 1.0 | 88 |

For the purpose of comparison, the same test was conducted by using 5 ml of a benzene solution (4.2×10$^{-3}$ mol/l) of a macrocyclic hexaketone (see "Tetrahedron Letters", No. 37, pp. 3,515-3,518) as a heavy metal ion capturing agent under the same conditions as said above. The results are shown below.

| Type of ions added | Concentration (g/l) | pH | Uranium concentration (ppm) Initial concentration | Residual conc. | Contact time (hr) | Capturing rate (%) |
|---|---|---|---|---|---|---|
| None |  | 8.0 | 10.0 | 0.23 | 20.0 | 97.7 |
| Mg++ | 1.29 | 8.0 | 10.0 | 1.60 | 3.5 | 84.0 |
| CO3-- | 0.14 | 8.0 | 10.0 | 5.25 | 3.5 | 47.5 |

The above-shown results show that said hexacarboxylic acid has excellent uranyl ion capturing ability and is capable of quantitatively capturing the uranyl ions even from a dilute solution with a concentration of order of ppm. It will be also noted that said hexacarboxylic acid is superior to hexaketone particularly in capturing of the uranyl ions in the presence of both magnesium ions and carbonate ions which are considered as the competitive ions in seawater.

Uranyl ion capturing test 2

68 mg of the compound of the formula (IV) obtained in the above-said process was added in 10 ml of an aqueous solution (pH 8.1) formed by dissolving 10.6 ppm of $UO_2(OCOCH_3)_2$ in distilled water, and the mixed solution was stirred. After 12 hours, said compound was filtered out and the amount of the residual uranium in the aqueous solution was measured. It was 0.27 ppm.

EXAMPLE 2

Preparation of bis(3-cyano-3-carboethoxypropoxy)ethane 5.28 g (0.11 mol) of sodium hydride was added to 50 ml of dry tetrahydrofuran, and to this solution was added dropwise a mixed solution of 12.2 g (0.11 mol) of ethyl cyanoacetate and 10.0 g (0.027 mol) of bis(2-iodoethoxy)ethane, followed by 2-hours reflux under heating. After the reaction, the most portion of tetrahydrofuran was distilled off and the residue was added with 10 ml of water, neutralized with 1N hydrochloric acid and extracted three times with 50 ml of ether. After drying the extract over anhydrous sodium sulfate, ether was distilled off and the resultant oily product was passed through a basic alumina (activity II)-packed column and eluted with petroleum ether-ether (1:4) to obtain 5.14 g of bis(3-cyano-3-carboethoxypropoxy)ethane,

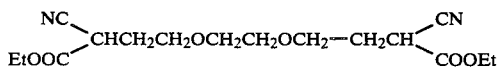

(yield: 56%). The property analyses of this compound gave the following results.

Infrared absorption spectrum (liquid film method): 2200 cm$^{-1}$ (C≡N stretching vibration), 1730 cm$^{-1}$ (C=O stretching vibration of ester).

Proton nuclear magnetic resonance (NMR) spectrum (solvent: CCl$_4$, internal standard Si(CH$_3$)$_4$): 4.2 (q, 4H), 3.9-3.4 (m, 10H), 2.5-1.9 (m, 4H), 1.3 (t, 6H).

Preparation of 2,2-bis[8-iodo-3,6-dioxaoctyl]cyanoacetic acid ethyl ester 1.71 g (0.036 mol) of sodium hydride was added to 40 ml of tetrahydrofuran dried with metallic sodium, and to this solution was added dropwise a mixed solution of 17.6 g (0.048 mol) of bis(2-iodoethoxy)ethane and 1.35 g (0.012 mol) of ethyl cyanoacetate, followed by 5-hours reflux under heating. Tetrahydrofuran was distilled off and the residue was cooled to room temperature, added with 1N hydrochloric acid until the litmus paper came to show acidity and then extracted three times with 50 ml of ether. After drying the extract over anhydrous sodium sulfate, ether was distilled off and the oily residue was passed through a basic alumina (activity II)-packed column and eluted with petroleum ether-ether (2:1) to obtain 3.43 g of 2,2-bis(8-iodo-3,6-dioxaoctyl)-cyanoacetic acid ethyl ester,

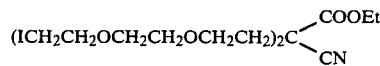

(yield: 48%).

IR absorption spectrum: 2200 cm$^{-1}$ (C≡N stretching vibration), 1730 cm$^{-1}$ (C=O stretching vibration of ester).

Proton NMR spectrum (solvent: CCl$_4$, internal standard: Si(CH$_3$)$_4$): 4.2 (q, 2H), 3.9-3.4 (m, 16H), 3.2 (t, 4H), 2.2 (t, 4H), 1.3 (t, 3H).

Preparation Example of tricyanotricarboxylic acid triethyl ester 0.19 g (4 mmol) of sodium hydride was added to 20 ml of dry tetrahydrofuran, and to this solution was added dropwise, while refluxing under heating, a solution formed by dissolving 0.6 g (1 mmol) of bis(8-iodo-3,6-dioxaoctyl)cyanoacetic acid ethyl ester obtained in the above-said preparation process and 0.34 g (1 mmol) of bis(3-cyano-3-carboethoxypropoxy)ethane in 20 ml of tetrahydrofuran, by using a specific dropping apparatus for the high dilution reactions (an apparatus designed to dilute the dropping solution with the refluxing solvent) over the period of 24 hours. After completion of said dropwise addition, reflux was continued for further 12 hours. After neutralizing the solution with dilute hydrochloric acid, tetrahydrofuran was distilled off and the residue was extracted with ether. Then ether was distilled off and the resultant oily residue was separated by basic alumina-packed column chromatography by using benzene-tetrahydrofuran (2:1) as eluent, obtaining 0.17 g of tricyanotricarboxylic acid triethyl ester (yield: 25%). The property analyses of this compound gave the following results.

Solubility: Easily soluble in chloroform, ether and benzene.

IR absorption spectrum: 2200 cm$^{-1}$ (C≡N stretching vibration), 1730 cm$^{-1}$ (C=O stretching vibration of ester).

Proton NMR spectrum (solvent: CDCl$_3$, internal standard, Si(CH$_3$)$_4$): 4.2 (q, 6H), 3.9-3.4 (m, 24H), 3.2 (t, 12H), 1.3 (t, 9H).

Preparation Example of 1,10,19-tricarboxy-1,10,19-tricyano-4,7,13,16,22,25-hexaoxacycloheptacosane 0.68 g (1 mmol) of tricyanotricarboxylic acid triethyl ester obtained in the above-said embodiment and 0.4 g (10 mmol) of sodium hydroxide were added to 10 ml of a 2:1 methanol/water solution and stirred for 12 hours. After termination of the reaction, methanol was distilled off and the residue was washed three times with 20 ml of ether and made acidic by adding dilute hydrochloric acid. After dissolving common salt in the water layer till saturation, the product was extracted five times with 50 ml of ether and the extract was dried over anhydrous sodium sulfate. Ether was then distilled off to obtain 0.48 g of a colorless liquid (yield: 80%). The results of the property analyses of this compound were as shown below.

Solubility: Soluble in ether and chloroform.

IR Absorption spectrum: 2200 cm$^{-1}$ (C≡N stretching vibration), 1690 cm$^{-1}$ (C=O stretching vibration of carboxylic acid).

Proton NMR spectrum (solvent: CDCl$_3$, internal standard Si(CH$_3$)$_4$): 10.8 (3H), 3.9-3.4 (m, 24H), 3.2 (t, 12H).

EXAMPLE 3

Preparation Example of 1,10-dicarboethoxy-1,10-bis(diethylphosphono)decane 0.96 g (0.02 mol) of sodium hydride was added to 20 ml of dry dimethylformamide, and to this solution was added dropwise a mixed solution of 4.48 g (0.02 mol) of ethyl diethylphosphonoacetate and 2.2 g (6 mmol) of 1,8-diiodooctane, the mixture being heated to 60° C. for 2 hours. After neutralizing the solution by adding 1N hydrochloric acid, dimethylformamide was mostly distilled off under reduced pressure and the residue was added with 10 ml of a saline solution and extracted three times with 50 ml of ether. After drying the extract over anhydrous sodium sulfate, ether was distilled off and the obtained oily product was refined by silica gel column chromatography by using benzene-ethyl acetate (1:1) as eluent obtaining 2.18 g of 1,10-dicarboethoxy-1,10-bis(diethylphosphono)decane,

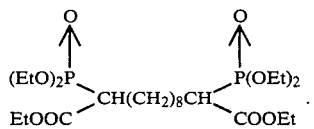

The property analyses of this compound gave the following results.

IR absorption spectrum (liquid film method): 1730 cm$^{-1}$ (C=O stretching vibration), 1250 cm$^{-1}$ (P=O stretching vibration), 1050 cm$^{-1}$, 1020 cm$^{-1}$ (C-O).

Proton NMR spectrum (solvent: CCl$_4$, internal standard: Si(CH$_3$)$_4$): 4.5-3.2 (m, 14H), 2.2-0.9 (m, 34H).

Preparation of 2,2-bis(8-iodooctyl)-diethylphosphonoacetic acid ethyl ester 0.96 g (0.02 mol) of sodium hydride was added to 40 ml of dry tetrahydrofuran, and to this solution was added dropwise under reflux a mixed solution of 1.34 g (6 mmol) of ethyl diethylphosphonoacetate and 11 g (0.03 mol) of 1,8-diiodooctane, and the solution was refluxed under heating for 4 hours. After distilling off tetrahydrofuran, the residue was cooled to room temperature, added with 1N hydrochloric acid until the litmus paper came to show acidity of the solution and then extracted three times with 50 ml of ether. After drying the extract over anhydrous sodium sulfate, ether was distilled off and the obtained oily residue was refined by passing through a basic alumina(activity II)-packed column using benzene-ethyl acetate (2:1) as eluent to obtain 1.76 g of 2,2-bis(8-iodooctyl)-diethylphosphonoacetic acid ethyl ester,

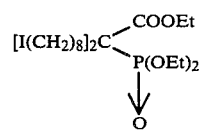

(yield: 42%).

IR absorption spectrum (liquid film method): 1720 cm$^{-1}$ (C=O stretching vibration of ester), 1245 cm$^{-1}$ (P=O stretching vibration), 1050 cm$^{-1}$, 1020 cm$^{-1}$ (C-O stretching vibration).

Proton NMR spectrum (solvent: CCl$_4$, internal standard Si(CH$_3$)$_4$): 4.4-4.0 (m, 6H), 3.3 (t, 4H), 2.0-1.0 (br, 35H).

Preparation of tricarboethoxy-tris(diethylphosphono)cycloheptacosane 0.19 g (4 mmol) of sodium hydride was added to 100 ml of dry tetrahydrofuran, and then a solution prepared by dissolving 0.56 g (1 mmol) of 1,10-dicarboethoxy-1,10-bis(diethylphosphono)decane and 0.7 g (1 mmol) of 2,2-bis(8-iodooctyl)-diethylphosphonoacetic acid ethyl ester, both obtained in the above-said processes, into 100 ml of tetrahydrofuran was added dropwise to said solution while refluxing under heating by spending a time of 24 hours. Upon completion of this dropwise addition, the solution was further refluxed for 12 hours, and then, after distilling off most of tetrahydrofuran, the solution was neutralized with dilute hydrochloric acid and extracted five times with 50 ml of ether. Thereafter, ether was distilled off and the residue was separated by silica gel column chromatography with benzene-tetrahydrofuran (2:1) as eluent to obtain 0.23 g of tricarboethoxy-tris(diethylphosphono)cycloheptacosane (yield: 23%). The results of the property analyses of this compound were as follows.

Solubility: Soluble in chloroform, dimethylformamide and dimethyl sulfoxide.

IR absorption spectrum: 1730 cm$^{-1}$ (C=O stretching vibration), 1250 cm$^{-1}$ (P=O stretching vibration), 1050 cm$^{-1}$, 1020 cm$^{-1}$ (C-O).

Proton NMR spectrum (solvent: CDCl$_3$, internal standard Si(CH$_3$)$_4$): 4.4-4.0 (m, 18H), 2.0-1.0 (br, 75H).

Preparation of 1,10,19-tricarboxy-1,10,19-triphosphonocycloheptacosane 0.1 g (0.1 mmol) of above-said tricarboethoxyl-tris(diethylphosphono)cycloheptacosane was heated with concentrated hydrochloric acid to obtain a hygroscopic solid product. Ester absorption disappeared from the IR absorption spectrum while absorption of phosphoric acid adn carboxylic acid were observed, indicating that the product had been hydrolyzed.

Solubility: Soluble in dimethylformamide and dimethyl sulfoxide.

IR absorption spectrum: 1690 cm$^{-1}$ (C=O), 1220 cm$^{-1}$ (P=O).

EXAMPLE 4

Preparation Example of bis(3,3-dicarboethoxypropoxy)ethane 5.28 g (0.11 mol) of sodium hydride was added to 50 ml of dry tetrahydrofuran, and to this solution was added dropwise a mixed solution of 17.6 g (0.11 mol) of diethyl malonate and 10.0 g (0.027 mol) of bis(2-iodoethoxy)ethane, followed by 2-hour reflux under heating. After the reaction, the most part of tetrahydrofuran was distilled off and the residue was added with 10 ml of water, neutralized by adding 1N hydrochloric acid and extracted three times with 50 ml of ether. After drying the extract, ether was distilled off and the oily product was passed through a silica gel packed column and eluted with petroleum ether-ether (4:1) to obtain 7.23 g of bis(3,3-dicarboethoxypropoxy)ethane, ($EtO_2C)_2CHCH_2CH_2OCH_2CH_2OCH_2CH_2CH(CO_2Et)_2$ (yield: 60%). The property analyses of this compound showed the following results.

IR absorption spectrum (liquid film method): 1725 $cm^{-1}$ (C=O stretching vibration of ester).

Proton NMR spectrum (solvent: $CCl_4$, internal standard $Si(CH_3)_4$): 4.1 (q, 8H), 3.9-3.4 (m, 10H), 2.5-1.9 (m, 4H), 1.3 (t, 12H).

Preparation of 2,2-bis(8-iodo-3,6-dioxacoctyl)malonic acid diethyl ester 1.71 g (0.036 mol) of sodium hydride was added to 40 ml of tetrahydrofuran dried over metallic sodium, and to this solution was added dropwise a mixed solution of 17.6 g (0.048 mol) of bis(2-iodoethoxy)ethane and 1.92 g (0.012 mol) of diethyl malonate, the mixture being refluxed under heating for hours. Tetrahydrofuran was distilled off and the residue was cooled to room temperature, added with 1N hydrochloric acid until the litmus paper came to indicate acidity and then extracted three times with 50 ml of ether. After drying the extract over anhydrous sodium sulfate, ether was distilled off and the oily residue was passed through a silica gel-packed column and eluted with petroleum ether-ether (2:1) to obtain 2.90 g of 2,2-bis(8-iodo-3,6-dioxaoctyl)malonic acid diethyl ester, $(ICH_2CH_2OCH_2CH_2OCH_2CH_2)_2C(CO_2Et)_2$ (yield: 38%).

IR absorption spectrum (liquid film method): 1730 $cm^{-1}$ (C=O stretching vibration of ester).

Proton NMR spectrum (solvent: $CCl_4$, internal standard: $Si(CH_3)_4$): 4.1 (q, 4H), 3.9-3.4 (m, 16H), 3.2 (t, 4H), 2.2 (t, 4H), 1.3 (t, 6H).

Preparation Example of hexaoxahexacarboxylic acid hexaethyl ester 3.22 g (5 mmol) of 2,2-bis(8-iodo-3,6-dioxaoctyl)malonic acid diethyl ester and 2.17 g (5 mmol) of bis(3,3-dicarboethoxypropxy)ethane, both obtained in the above-said processes, were dissolved in 1,000 ml of dry tetrahydrofuran, and this solution was further added with 0.96 g (20 mmol) of sodium hydride and refluxed under heating for 24 hours. After neutralizing the solution with dilute hydrochloric acid, tetrahydrofuran was distilled off, followed by ether extraction. After drying the extract over anhydrous sodium sulfate, ether was distilled off and the oily residue was separated by silica gel column chromatography using petroleum ether-ether (1:2) as eluent to obtain 1.88 g of hexaoxahexacarboxylic acid hexaethyl ester (yield: 46%). The property analyses of this compound gave the following results.
Solubility: Easily soluble in chloroform, ether and benzene.

IR absorption spectrum (liquid film method): 1725 $cm^{-1}$ (C=O stretching vibration of ester).

Proton NMR spectrum (solvent: $CCl_4$, internal standard: $Si(CH_3)_4$): 3.9 (q, 12H), 3.4-3.1 (m, 24H), 2.1 (t, 12H), 1.2 (t, 18H).

Preparation Example of 1,1,10,10,19,19-hexacarboxy-4,7,13,16,22,25-hexaoxacycloheptacosane 0.82 g (1 mmol) of hexaoxahexacarboxylic acid hexaethyl ester obtained in the above-said process was added to 10 ml of a 2:1 methanol/water mixture containing 0.4 g (10 mmol) of sodium hydroxide, and the solution was refluxed under heating for 12 hours. After the reaction, methanol was distilled off and the remaining solution was washed three times with 20 ml of ether and made acidic by adding dilute hydrochloric acid. Then water was distilled off under reduced pressure and the residue was extracted three times with 100 ml of acetone. After drying the extract over anhydrous sodium sulfate, acetone was distilled off and the oily residue was further extracted three times with 200 ml of ether. The extract was dried over anhydrous sodium sulfate and then ether was distilled off to obtain 0.47 g of 1,1,10,10,19,19-hexacarboxy-4,7,13,16,22,25-hexaoxacycloheptacosane (yield: 72%). The results of the property analyses of this compound were as shown below.
Solubility: Soluble in water, ether and alcohol.

IR absorption spectrum (liquid film method): 1705 $cm^{-1}$ (C=O stretching vibration of carboxylic acid).

Proton NMR spectrum (solvent: $D_2O$): 3.9-3.4 (m, 24H), 1.9 (t, 12H).

What is claimed is:

1. A macrocyclic compound of formula (I)

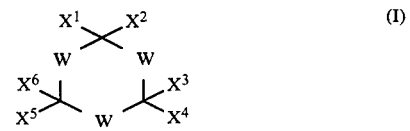

wherein $X^1$, $X^3$ and $X^5$ are individually taken from the first class consisting of —COOH,

—$SO_3H$, —$PO_3H_2$ and —$PO_4H_2$; and $X^2$, $X^4$ and $X^6$ are individually taken from the class consisting of said first class hydrogen, alkyl having 1-18 carbon atoms, phenyl, —$COOR^2$,

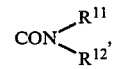

—$COR^1$, —CN, —$SOR^2$,

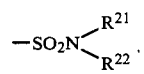

—$SO_2R^2$, —$NO_2$, —$PO_3R^{21}R^{22}$ and —$PO_4R^{21}R^{22}$; wherein $R^1$ is hydrogen, an alkyl having 1-18 carbon atoms, or a phenyl group, $R^2$ is an alkyl having 1-18 carbon atoms or a phenyl group, $R^{11}$ and $R^{12}$ are individually selected from the same group as $R^1$, and $R^{21}$ and $R^{22}$ are individually selected from the same group as $R^2$; and W is a divalent group taken from —$(CH_2)_n$— wherein n=2-18 and wherein 0-9 ($CH_2$) groups have been replaced by a moiety selected from the group consisting of O, S, N—H, provided that any hetero atoms appearing within W are separated from each other by at least two carbon atoms and that the two terminal atoms of each W which are linked to non-W atoms of said compound are carbons.

2. The macrocyclic compound of claim 1 wherein

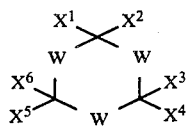   (I)

wherein $X^1$, $X^3$ and $X^5$ are individually taken from the first class consisting of —COOH,

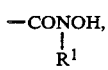

—$SO_3H$, —$PO_3H_2$ and —$PO_4H_2$; and $X^2$, $X^4$ and $X^6$ are individually taken from the class consisting of said first class hydrogen, alkyl having 1-4 carbon atoms, phenyl, —$COOR^2$,

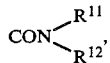

—$COR^1$, —CN, —$SOR^2$,

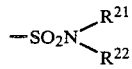

—$SO_2R^2$, —$NO_2$, —$PO_3R^{21}R^{22}$ and —$PO_4R^{21}R^{22}$; wherein $R^1$ is hydrogen, an alkyl having 1-18 carbon atoms, or a phenyl group, $R^2$ is an alkyl having 1-18 carbon atoms or a phenyl group, $R^{11}$ and $R^{12}$ are individually selected from the same group as $R^1$, and $R^{21}$ and $R^{22}$ are individually selected from the same group as $R^2$.

3. The compounds of claim 1 wherein n=6 to 10.
4. The compounds of claim 3 wherein n=7 to 9.
5. The compounds of claim 4 whererin n=8.
6. The compounds of claim 1 wherein W is —$(CH_2)_n$— or —$(CH_2)_2Y(CH_2)_2Y(CH_2)_2$— wherein Y is O, S or N—H.
7. The compounds of claim 6 wherein Y is O.

8. The compounds of claim 1 wherein $X^1$, $X^3$, and $X^5$ are —COOH and $X^2$, $X^4$, and $X^6$ are individually selected from —COOH, —$COO(CH_2CH_3)$, —CN, and —$PO_3(CH_2CH_3)_2$.

9. A macrocyclic compound as defined in claim 1, wherein the compound represented by the above-shown general formula (I) is 1,1,10,10,19,19-hexacarboxy-cycloheptacosane represented by the following chemical formula:

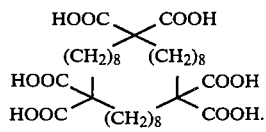

10. A macrocyclic compound as defined in claim 1, wherein the compound represented by the above-shown general formula (I) is 1,10,19-tricarboxy-1,10,19-tricyano-4,7,13,16,22,25-hexaoxacycloheptacosane represented by the following chemical formula:

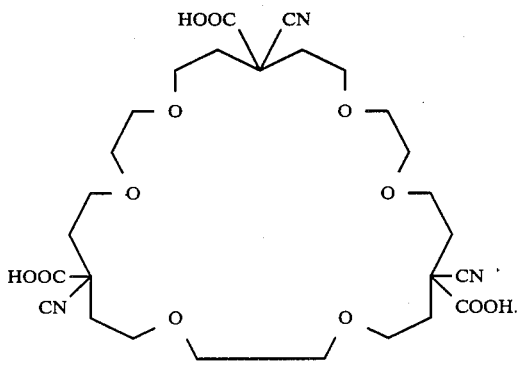

11. A macrocyclic compound as defined in claim 1, wherein the compound represented by the above-shown general formula (I) is 1,10,19-tricarboxy-1,10,19-triphosphonocycloheptacosane represented by the following chemical formula:

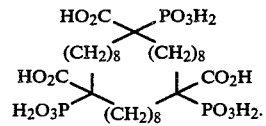

* * * * *